United States Patent [19]

Schleigh et al.

[11] Patent Number: 5,118,695

[45] Date of Patent: Jun. 2, 1992

[54] 1-HYDROXYINDOLE FUNGICIDES

[75] Inventors: William R. Schleigh, Brockport; Thomas R. Welter, Webster, both of N.Y.

[73] Assignee: Eastman Kodak Company, Rochester, N.Y.

[21] Appl. No.: 562,998

[22] Filed: Aug. 6, 1990

[51] Int. Cl.⁵ .............................................. A01N 43/38
[52] U.S. Cl. ...................................... 514/339; 514/415; 514/419; 546/273; 548/492; 548/493; 548/505; 548/509; 548/511
[58] Field of Search ................ 548/505, 469; 514/415, 514/419, 339

[56] References Cited

U.S. PATENT DOCUMENTS

| | | | |
|---|---|---|---|
| 3,296,277 | 1/1967 | Petracek | 548/505 |
| 3,839,557 | 10/1974 | Richter et al. | 514/415 |
| 3,939,178 | 2/1976 | Demerson et al. | 548/510 |
| 4,069,230 | 1/1978 | Morooka et al. | 548/505 |
| 4,506,078 | 3/1985 | Batcho | 548/469 |
| 4,590,271 | 5/1986 | Daluge et al. | 548/465 |
| 4,742,077 | 5/1988 | Stütz | 548/486 |
| 4,812,162 | 3/1989 | Anthony et al. | 548/505 |

FOREIGN PATENT DOCUMENTS 0151505 5/1979 Japan.

OTHER PUBLICATIONS

Hazard et al., *Bull. Soc. Chim. Fr.*, 1974, pp. 121-125.
Acheson et al., *J. Chem. Soc. (C)*, 1970, pp. 1067-1070.
Acheson et al., *J. Chem. Soc. (C)*, 1968, pp. 504-507.
Sword, *Chem. Ind.*, 1972, p. 166.
Sword, *J. Chem. Soc. (C)*, 1970, pp. 1916-1922.
Bernard et al., *Tetrahedron Letters*, No. 44, pp. 4529-4532 (1972).
Louden et al., *J. Chem. Soc.*, 1960, pp. 3462-3466.
*J. Agric. Food Chem.*, 23(4), 785(1975) by Dekker, H. A. Selling and J. C. Overeem.
E. Fischer and H. Hutz, *Chem. Ber.*, 28, 585(1985).

*Primary Examiner*—Richard L. Raymond
*Assistant Examiner*—Scott C. Rand

[57] ABSTRACT

1-Hydroxyindoles of the following formula are useful in controlling fungi:

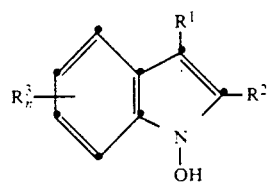

wherein:

$R^1$ is hydrogen or an electron withdrawing group;
$R^2$ is selected from the group consisting of alkenyl having 2-10 carbon atoms, N-substituted-α-iminobenzyl, an unsubstituted or substituted aromatic group and acyl of 2-16 carbon atoms.
$R^3$ is selected from the group consisting of halogen atoms, and
n is 0 to 4.

9 Claims, No Drawings

1-HYDROXYINDOLE FUNGICIDES

FIELD OF THE INVENTION

The present invention relates to fungicides.

CROSS-REFERENCE TO RELATED APPLICATION

Reference is hereby made to commonly assigned copending U.S. patent application Ser. No. 07/562,997, entitled "2-Substituted-1-Hydroxyindoles", filed on even date herewith in the names of T. R. Welter and William R. Schleigh, now abandoned.

BACKGROUND OF THE INVENTION

In view of world hunger, it is useful to provide the public with a variety of fungicides for use in food agriculture.

Of the 1-hydroxyindoles known in the art, U.S. Pat. No. 3,296,277 dated Jan. 3, 1967 and entitled "Substituted 3-Cyano-1-hydroxy-2-phenylindoles, assigned to Rexall Drug and Chemical Company, Los Angeles, Calif., discloses the compounds 3-cyano-1-hydroxy-2-(o-nitrophenyl)indole and 3-cyano-1-hydroxy-2-(p-methoxyphenyl)indole. The Rexall patent also discloses the use of compounds bearing nitrophenyl or lower alkoxyphenyls as active central nervous system depressants and adrenolytic agents.

While the general structure of 1-hydroxy-2-indoles is known in the art, the fungicidal use of 1-Hydroxyindoles in general has not been disclosed to date. Indeed, "Structure-Activity Relationships of Some Antifungal Indoles", J. Agric. Food Chem., 23(4), 785(1975) by W. H. Dekker, H. A. Selling and J. C. Overeem reports that substitution on the indole nitrogen cancels out fungicidal activity almost completely.

A disclosure by Japanese workers at Kuraray Co., Ltd. reported in Kokai 80-151, 505, November, 1980 contains a disclosure of a series of indole fungicides which included several active N-substituted indoles. Of the active N-substituted indoles reported, none had oxygen substituents.

SUMMARY OF THE INVENTION

The present invention relates to a process for controlling fungus which comprises contacting said fungus with a fungicidally effective amount of 1-hydroxyindoles having the following formula:

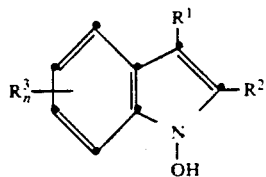

wherein
$R^1$ is hydrogen or an electron withdrawing group,
$R^2$ is selected from the group consisting of alkenyl having 2-10 carbon atoms, N-substituted-α-iminobenzyl, an unsubstituted or substituted aromatic group, and acyl having 2-16 carbon atoms
$R_n^3$ is selected from the group consisting of halogen atoms, and
n is 0 to 4.

In another aspect of the invention, a compound useful in the process as described above is provided comprising the structure as shown above wherein
$R^1$ is cyano or hydrogen,
$R^2$ is selected from the group consisting of alkenyl having 2-10 carbon atoms, N-substituted-α-iminobenzyl, an unsubstituted or substituted aromatic group and acyl having 2-16 carbon atoms.
$R_n^3$ is selected from the group consisting of halogen atoms, and
n is 0 to 4,

DETAILED DESCRIPTION OF THE PREFERRED EMBODIMENTS

Foliar phytopathogenic fungi are controlled by applying a fungicidally effective amount of compounds of formula

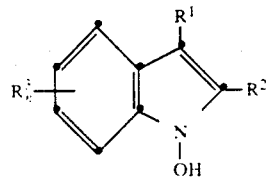

wherein
$R^1$ is hydrogen or an electron withdrawing group such as carbamoyl, for example, carbamoyl, t-butylcarbamoyl and dimethylcarbamoyl, carboxy, nitro, cyano and so on.

$R^2$ is selected from the group consisting of alkenyl having 2-10 carbon atoms, such as vinyl, allyl or butenyl, N-substituted-α-iminobenzyl groups, i.e., wherein the imino nitrogen is substituted, preferably with a phenyl, anilino or dimethylamino group, for example, α-(phenylimino)benzyl, α-(anilinoimino)benzyl and α-(dimethylaminoimino)-benzyl, an unsubstituted or substituted aromatic group having 5-6 nuclear atoms in the aromatic ring, such as phenyl, nitrophenyl, trifluoromethylphenyl, tolyl, 4-methoxyphenyl, 4-phenylsulfonylphenyl, 4-benzophenonyl, 4-t-butylphenyl, chlorophenyl, 4-(2-cyanovinyl)phenyl, bromophenyl, 4-(2-carboxyvinyl)phenyl, dichlorophenyl, fluorophenyl, formylphenyl, hydroximinomethylphenyl, carboxymethylphenyl, carboxyphenyl, hydroxyphenyl, sulfamoylphenyl, acetylphenyl, cyanophenyl, 2-furyl, 4-carbamoylphenyl, 2-furanyl, 4-t-butylphenyl, pyridyl, dimethoxyphenyl, etc. and acyl having 2-16 carbon atoms, for example, alkylcarbonyl wherein the alkyl group has about 1-16 carbon atoms, or arylcarbonyl wherein said aryl group has about 5-16 carbon atoms, for example, 2,2-dimethylpropionyl (i.e., neopentanoyl), acetyl, butyryl, octanoyl, benzoyl, 3,4-dichlorobenzoyl, 4-methylbenzoyl, 4-bromobenzoyl, 3-trifluoromethylbenzoyl, chlorobenzoyl, 3,4-dimethoxybenzoyl, 4-methoxybenzoyl, and so on.

$R_n^3$ is selected from the group consisting of halogen atoms, such as chloro, bromo, iodo, fluoro, and
n is 0 to 4 and it is understood that when n is less than 4, hydrogen fills the unsubstituted positions.

Preferred methods of the invention utilize compounds having the above structure wherein
$R^1$ is cyano or hydrogen and $R^2$, and $R^3$ are as described above.

Other preferred methods of the invention utilize compounds having the above structure wherein $R_1$ is cyano.

$R^2$ is selected from the group consisting of 4-nitrophenyl, 3-nitrophenyl, 3-trifluoromethylphenyl, 4-methoxyphenyl, 4-fluorophenyl, 4-formylphenyl, 4-carbamoylphenyl, 2-furyl, vinyl, 4-pyridyl, 2-pyridyl, phenyl, 3,4-dichlorophenyl, 4-methylphenyl, 4-bromophenyl, 4-chlorophenyl, 3,4-dimethoxyphenyl, 4-methoxyphenyl, 3-trifluoromethylbenzoyl, 4-t-butylphenyl, hydroxyiminomethylphenyl, and α-(phenylimino)benzyl, $R_n{}^3$ where n is 0 and represents no substituents at $R^3$.
n is 0.

Further preferred methods of the invention utilize compounds having the above structure wherein
$R^1$ is cyano, $R^2$ is selected from the group consisting of alkenyl having 2-10 carbon atoms, N-substituted α-iminobenzyl, an unsubstituted or substituted aromatic group and acyl having 2-16 carbon atoms, and n is 0, or $R^1$ is cyano, $R^2$ is selected from the group consisting essentially of phenyl and 4-nitrophenyl, and n is 0, or $R^1$ is hydrogen.

$R^2$ is selected from the group consisting essentially of phenyl, 4-nitrophenyl and 4-chlorophenyl.

$R_n{}^3$ where n = 0-2 and R is selected from chloro, so that $R_n{}^3$ represents chloro, dichloro or no substituents replacing hydrogen for $R^3$.

The most preferred methods of the invention utilize compounds having the above structure wherein:

$R^2$ is a para- or meta- substituted phenyl group, preferably 3-nitrophenyl or 4-nitrophenyl.

Further, a fungicidal composition is provided comprising a fungicidally effective amount of at least one of the following active ingredients:

3-cyano-1-hydroxy-2-(4-nitrophenyl)indole,
3-cyano-1-hydroxy-2-phenylindole,
3-cyano-1-hydroxy-2-(3-nitrophenyl)indole,
3-cyano-1-hydroxy-2-(4-trifluoromethylphenyl)indole,
3-cyano-1-hydroxy-2-(3-trifluoromethylphenyl)indole,
3-cyano-1-hydroxy-2-(4-methoxyphenyl)indole,
3-cyano-1-hydroxy-2-(4-benzoylphenyl)indole,
3-cyano-1-hydroxy-2-[4-(2-cyanovinyl)phenyl]indole,
3-cyano-2-(3,4-dichlorophenyl)-1-hydroxyindole,
3-cyano-5,6-dichloro-1-hydroxy-2(4-nitrophenyl)indole,
6-chloro-3-cyano-1-hydroxy-2-(4-nitrophenyl)indole,
3-cyano-5,6-dichloro-1-hydroxy-2-phenylindole,
6-chloro-3-cyano-1-hydroxy-2-phenylindole,
3-cyano-2-(2-furyl)-1-hydroxyindole,
3-cyano-2-vinyl-1-hydroxyindole,
3-cyano-1-hydroxy-2-(4-pyridyl)indole,
3-cyano-1-hydroxy-2-(2-pyridyl)indole,
1-hydroxy-2-phenylindole,
6-chloro-1-hydroxy-2-(4-chlorophenyl)indole,
2-Benzoyl-3-cyano-1-hydroxyindole,
3-cyano-2-(3,4-dichlorobenzoyl)-1-hydroxyindole,
3-cyano-1-hydroxy-2-(p-toluoyl)indole,
2-(4-Bromobenzoyl)-3-cyano-1-hydroxyindole,
3-cyano-1-hydroxy-2-(3-trifluoromethylbenzoyl)indole,
2-(4-chlorobenzoyl)-3-cyano-1-hydroxyindole,
3-cyano-2-(3,4-dimethoxybenzoyl)-1-hydroxyindole,
3-cyano-1-hydroxy-2-(4-methoxybenzoyl)indole,
2-benzoyl-5-chloro-3-cyano-1-hydroxyindole,
3-cyano-1-hydroxy-2-neopentanoylindole,
3-cyano-2-(4-fluorophenyl)-1-hydroxyindole and
3-cyano-2-(4-formylphenyl)-1-hydroxyindole,
3-cyano-1-hydroxy-2-(α-phenyliminobenzyl)indole,
3-cyano-1-hydroxy-2-(α-phenylazino)indole and
3-cyano-2-(α-dimethylazinobenzyl)-1-hydroxyindole.

Typical compounds representative of those useful in the present invention include the compounds listed above as active ingredients in the fungicidal compositions of the invention.

The present invention provides a means for controlling wheat leaf rust and other fungi.

The N-hydroxyindoles are generally obtainable as colorless to yellow crystalline materials having characteristic melting points and absorption spectra and which may be purified by recrystallization from common organic solvents. They are appreciably soluble in many organic solvents such as methanol, ethanol, acetone, chloroform, benzene, dioxane, dimethyl sulfoxide and N,N-dimethylformamide, but are relatively insoluble in water.

The compounds of the invention can be prepared in general through minor modifications of literature procedures.

The synthesis of N-hydroxy-3-cyano-2-phenylindole was first described by Loudon and Tennant in J. Chem. Soc., 3466(1960). This preparation is represented by the following reaction scheme:

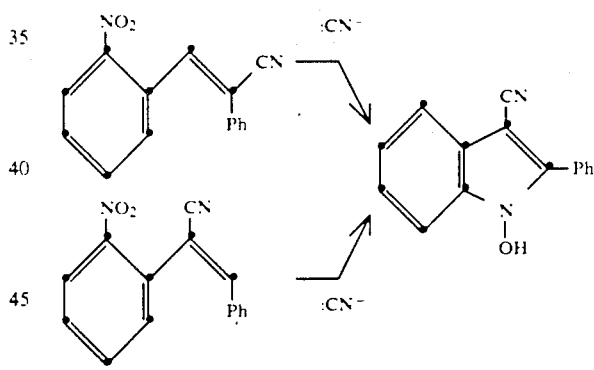

The preparation involved the cyanide induced cyclization of either of two 2-nitrophenyl-substituted cyanostilbenes.

Further development towards the preparation of 1-Hydroxyindoles is seen in the work of F. J. Petracek shown in U.S. Pat. No. 3,296,277 entitled "Substituted 3-Cyano-1-Hydroxy-2-Phenylindoles which discloses the preparation of indoles containing substituted phenyls as seen in the following reaction scheme:

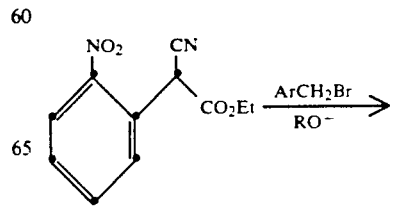

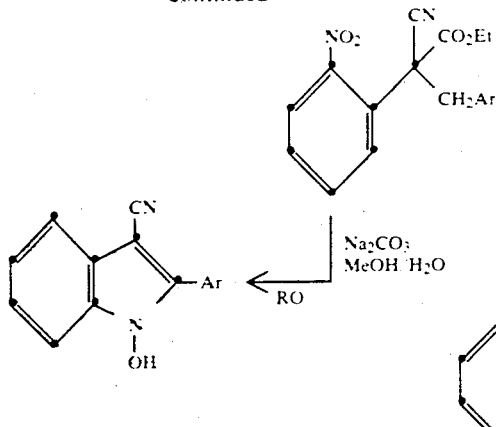

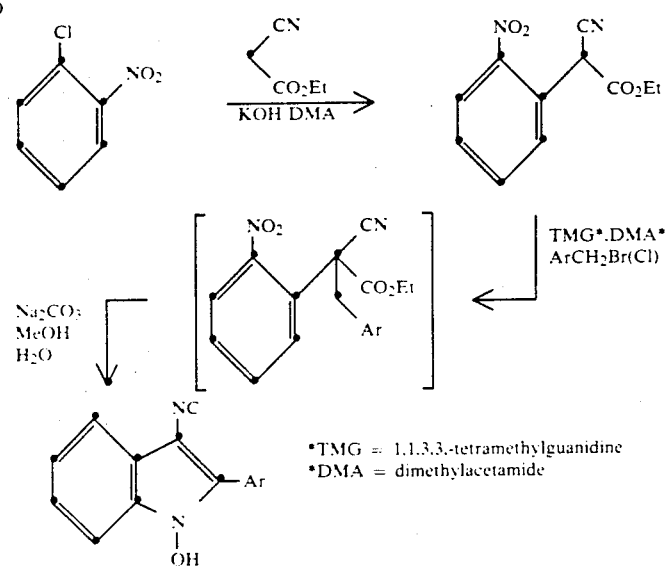

This synthesis involves the condensation of ethyl 2-nitrophenylcyanoacetate with various benzyl halides under basic conditions followed by aqueous alkaline rearrangement providing 2-aryl-3-cyano-1-hydroxyindoles. The free hydroxyl group is preferred for activity. Other compounds can be prepared by the acid rearrangement of the well known benzoin oximes through the method described by E. Fischer in Chemische Berichte. 28.585(1885).

The compounds used in the invention can be prepared by using a slight modification of the method of Petracek as discussed hereinabove in reference to U.S. Pat. No. 3,296,277. 2-Chloronitrobenzene can be condensed with ethyl cyanoacetate in the presence of excess potassium hydroxide affording a good yield of the ethyl 2-cyano-2-nitrophenylacetate as can be seen by the following reaction scheme:

Various benzyl halides can then be condensed with the acetate ester followed by cyclization to the aryl-substituted indole as shown. Bromides are preferred.

A series of 2-keto derivatives were also prepared through the method of Loudon and Tennant previously described wherein: N-hydroxy-2-benzoyl-3-cyanoindole was prepared by cyano addition-cyclization of 1-(2-nitrophenyl)-3-phenyl-1-propen-3-one (2-nitrochalcone). Various 2-nitrochalcones could be prepared via condensation of 2-nitrobenzaldehydes with acetophenones. Thus, the series of 2-keto derivatives was prepared as exemplified by the following scheme:

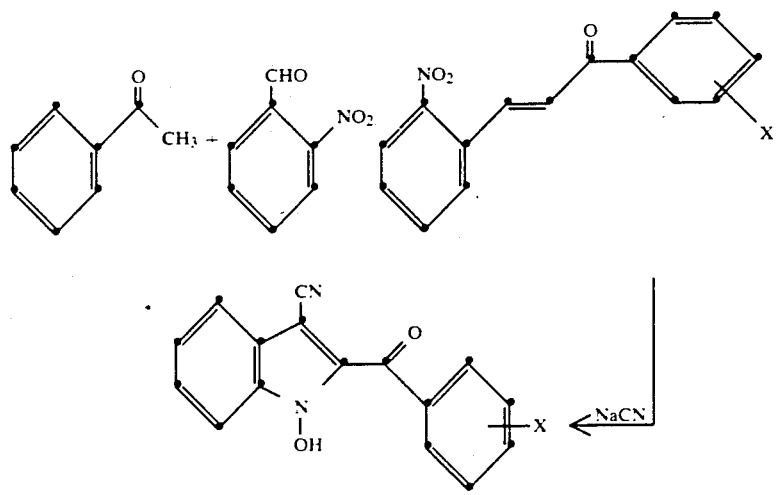

The preferred 2-acyl compounds useful in the process of this invention are
2-benzoyl-3-cyano-1-hydroxyindole;
3-cyano-2-(3,4-dichlorobenzoyl)-1-hydroxyindole;
3-cyano-1-hydroxy-2-(p-toluoyl)indole;
2-(4-bromobenzoyl)-3-cyano-1-hydroxyindole; and
2-(4-chlorobenzoyl)-3-cyano-1-hydroxyindole.

The 1-hydroxyindoles used in the invention can be applied as fungicidal sprays by methods commonly employed at varying concentrations, air-blast, aerial sprays and dusts. The dilution and rate of application will depend upon the type of equipment employed, the method and frequency of application desired and diseases to be controlled.

Such active compounds may be employed alone or in the form of mixtures with such solid and/or liquid carrier vehicles and/or with other known compatible active agents, especially plant protection agents, such as other insecticides, nematocides, or acaricides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The process of the present invention is useful for the control of wheat leaf rust and can be utilized on the foliage. For such purposes, these compounds can be used in solutions, liquid formulations, or dry powder formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's Emulsifiers and Detergents/Functional Materials and McCutcheon's Functional Materials all published annually by McCutcheon Division of MC Publishing Company (New Jersey).

In general, the compounds utilized in this invention can be dissolved in appropriate solvents such as acetone, methanol, ethanol, dimethylformamide or methyl sulfoxide and such solutions extended with water. The concentration of the solution can vary from 1 to 90% with a preferred range being (5 to 50%).

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10 to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations varies widely.

Dusts are prepared by mixing the 1-hydroxyindoles and salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

The compounds of the invention were particularly tested for activity against *Colletotrichum lagenarium* (Anthracnose on cucumbers), *Puccinia recondita* (wheat leaf rust), *Erisiphe polygoni* (powdery mildew on beans), *Phytophthora infestans* (late blight on tomatoes), *Rhizoctonia solani* (Rhizoctonia on cotton), Pythium sp. (damping off on peas), and *Botrytis cinerea* (gray mold). They showed particularly enhanced activity against rust disease, including *Puccinia recondita* (wheat leaf rust).

EXAMPLE I

The compounds used in this invention were evaluated as protectant fungicides by standard methods A and B. The results of these primary evaluations are recorded in Table I and some in Table V. Furthermore, certain of the compounds were evaluated for their dose response profiles against wheat leaf rust. The procedure was the same as procedure A with the exception that various levels of test compound were applied as described in Step 18.

METHOD A

Evaluation of Test Compounds for Control of Foliar Pathogens

Five pathogens are used for evaluating potential fungicides. Refer to Table A-1 for specific protocol of each test.

1. Host plants are grown in 13.3×13.3 cm. units held in standard greenhouse flats (52×26×6 cm). The soil used is steam-sterilized sandy loam. Plants are grown to the appropriate stage and then treated with the test chemical.

2. Ten mL of the test solution containing 500 ppm active ingredient (AI) per mL is applied per unit sample. The appropriate amounts of chemical per unit is calculated as follows:

$$\frac{0.05 \times 10}{100} = \text{grams of chemical per } 13.3 \times 13.3 \times 6 \text{ cm unit}$$

where;

0.05=500 ppm converted to percent,
10=mL of diluent, and
100=percent AI (active ingredient) of chemical sample, in this case, it is 100% or technical grade.

3. A solution of an octylphenoxy polyethoxy ethanol non-ionic surfactant sold by Rohm & Haas Co. as Triton X-100 in acetone (1000 ppm w/v) is used to dissolve the material under test. The solution is diluted with distilled water 1:9 v/v to obtain a final mixture of 10% acetone and 100 ppm of Triton X-100 non-ionic surfactant in water. Further dilution of this stock solution, as required in rate studies, is done by using a diluent consisting of 100 ppm Triton X-100 non-ionic surfactant in water so that a constant concentration of the surfactant is maintained at all levels.

4. The test consists of:
   A. Untreated control
   B. Test
   C. Standard

5. The standards (Table A-I) are applied at the given rate. Some lesions may occur at these rates.

6. Two replicates per test.

7. Test compounds are applied at 1.4 kgf/cm² using a hand-held spray gun. The plants are rotated on a turn table during application to assure even coverage.

8. Following spraying, the foliage is air dried.

9. Bean plants are then placed adjacent to mildew-infested beans. After 24 hours exposure, the plants are moved to the opposite end of the greenhouse and held until mildew first appears on the control. The test compound is then evaluated. The plants are further held until 100% leaf infection occurs in the control, and a final readout is taken.

10. The remaining test plants: tomatoes, cucumbers and wheat are inoculated with the respective pathogen (Table A-I). Spores are obtained from culture plates and diluted in 1% glucose plus 1 drop of polyoxyethylene (20) sorbitan monolaurate (Tween 20) per 100 mL of solution. Spores are sprayed over the plant foliage at 10 θ using a spray atomizer. Fifteen mL of spray is applied per greenhouse flat (i.e., 8 units).

11. Following inoculation, the plants are placed into an incubation chamber for 48 hours. Tomatoes inoculated with *P. infestans* are held at 20° C. and 100% RH. All others are held at 25° C. and 100% RH. The humidity is maintained by an overhead sprayer which produces fine mist for 15 seconds every 15 minutes.

12. Following incubation, the plants are placed on a greenhouse bench. An overhead misting unit continues to wet the foliage for 15 seconds every 15 minutes.

13. The activity of the test compound is then evaluated when lesions first appear in the control; generally in 2 to 3 days. The plants are then held until 100% leaf infection occurs in the control, and a final readout is taken.

14. The following information is recorded:
   A. Number of healthy plants
   B. Number of diseased plants
   C. Number of lesions
   D. Phytotoxicity, i.e., chlorosis, marginal leaf burning, stunting, unusual growth patterns, etc.

15. The percentage disease control is calculated according to the following formula:

$$MPDC = \frac{MDIC - MDIT}{MDIC} \cdot 100$$

where:
MPDC = mean percentage of disease control,
MDIC = mean percentage of disease incidence in the untreated control, and
MDIT = mean percentage of disease incidence in the treatment.

16. Based on the percentage of disease control, treatments are ranked 0 to 4 using the following scale:

| % Control | Ranking |
|---|---|
| 0-9 | 0 |
| 10-29 | 1 |
| 30-49 | 2 |
| 50-79 | 3 |
| 80-100 | 4 |

These primary screening results are recorded in Table I.

17. Compounds which facilitate 50% or better control (ranking of 3 or 4) are recommended for secondary screening.

18. Secondary screening consists of rate studies using 250, 500, 1000 and 2000 ppm for compounds ranked as 3. Those ranked as 4 are tested at 125, 250, 500 and 1000 ppm. Occasionally, compounds with a 2 ranking will be tested at 500, 1000, 2000 and 4000 ppm if the few healthy plants are relatively disease-free. From these data are determined and reported the $EC_{50}$'s, i.e., the concentrations at which 50% control of the fungus is observed. These secondary screening results are reported in Tables II to V for wheat leaf rust.

TABLE A-I

| Pathogen | Common Name | Host | Host Stage | No. Plants/ Unit | Inoculation Level | Standard | (ppm AI) |
|---|---|---|---|---|---|---|---|
| *Colletotrichum lagenarium* | Anthracnose | Cucumber (Nat'l Pickling var.) | First leaf | 10 | 1.3 × 10⁶ spores/mL | Benomyl | 520 |
| *Puccinia recondita* | Wheat Leaf Rust | Wheat (Anza. var.) | 10 cm high | 300 | 250 mg spores/100 mL | Triadimefon | 600 |
| *Erysiphe polygoni* | Powdery Mildew | Bean (Green Crop Bush var.) | First leaves | 10 | 24 hr. exp. to infected plants | Triadimefon | 75 |
| *Phytophthora infestans* | Late Blight | Tomato (Red Cherry var.) | First leaf | 50 | 1.3 × 10⁴ spores/mL | Chlorothalonil | 260 |

METHOD B

Evaluation of Test Compounds for Control of *Rhizoctonia solani*

1. Sandy loam soil is steam-sterilized at 190° F. (87.8° C.) for 48 hours. The soil is then removed and allowed to cool. After cooling 24 hours, the soil generally has a moisture content of about 5 to 8 percent.

2. Soil is mixed to insure uniform composition and moisture.

3. Three 150 gram samples of soil are removed, weighed and placed into an oven at 100° F. (27.8° C.) and allowed to dry for one hour. The approximate percent dry weight is then calculated. This calibration is used to estimate the dry weight of the soil lot.

4. One gallon (approximately 4293.2 grams fresh wt.) of soil is mixed with 3 core samples from Rhizoctonia culture plate. A core sample is a 3.0 cm diameter disc of spores, mycelium, mixed in vermiculite. It is cut using the mount of a test tube. The sample weighs about 3.2 grams. Samples are taken from the margins of fungal growth from plates 4 to 6 weeks old.

5. The mycelium and spores are uniformly distributed throughout the soil sample by hand mixing the soil for 5 minutes.

6. One hundred and fifty grams dry weight (equivalent) of soil are then placed into 10 ounce styrofoam cups.

7. Ten milliliters of test solution containing 50 ppm w/v is added to the soil sample. The appropriate amount of chemical per container is calculated as follows:

$$\frac{.005 \cdot 150}{100} = \text{grams of chemical per } 13.3 \cdot 13.3 \cdot 6 \text{ cm unit}$$

where:
0.005 = 50 ppm converted to percent
150 = dry weight of soil sample, and
100 = percent AI of chemical sample.

8. A solution of Triton X-100 non-ionic surfactant in acetone (1000 ppm w/w) is used to dissolve the material under test and the solution is diluted with distilled water 1:9 v/v to obtain a mixture of 10 percent acetone and 100 ppm of Triton X-100 nonionic surfactant in water. Further dilution of this stock solution, as required in rate studies, is done by using a diluent consisting of 100 ppm Triton X-100 nonionic surfactant in water so that a constant concentration of the surfactant is maintained at all levels.

9. A test consists of:
A. Control—seed only
B. Control—seed plus inoculum
C. Test—seed plus compound
D. Test—seed plus compound plus inoculum
E. Standard 10. The standard, Tersan SP (chloroneb), is tested at 50 ppm AI w/w.

11. Two replicates of each test are conducted.

12. Following application of the chemical, the cups are capped and vigorously shaken to mix the chemical throughout the soil sample.

13. A tablespoon of soil is then temporarily removed and 10 cotton seeds planted beneath. The soil surface is tamped smooth. Ten milliliters of water added to the surface and the cup again sealed.

14. The sealed cups are held at 70° F. (21.1° C.) for 3 days to allow germination. The cups are then uncapped and placed under fluorescent lights for an additional 11 days.

15. The plants are uprooted and examined. If the primary root has one or more lesions, the plant is considered diseased. The following information is recorded:
A. Number healthy plants
B. Number diseased plants
C. Phytotoxicity, i.e., chlorosis, root stunting, unusual growth patterns, etc.

16. The percent healthy plants in each treatment is adjusted to account for natural mortality using Abbott's formula:

$$\frac{NHC - NHT}{NHC} \cdot 100 = APM$$

where,
APM = adjusted percentage mortality,
NAC = number healthy plants in control (no inoculum, no fungicide), and
NHT = number healthy plants in treatment.

17. The percentage disease control is calculated according to the following formula:

$$\frac{DIC - DIT}{DIC} \cdot 100 = PDC$$

where,
PDC = percentage of disease control
DIC = disease incidence in control (no fungicide), and
DIT = disease incidence in treatment.

18. Based on the percentage of disease control, treatments are ranked 0 to 4 using the following scale:

| % Control | Ranking |
| --- | --- |
| 0-9 | 0 |
| 10-29 | 1 |
| 30-49 | 2 |
| 50-79 | 3 |
| 80-100 | 4 |

The primary test results are recorded in Table I.

TABLE I

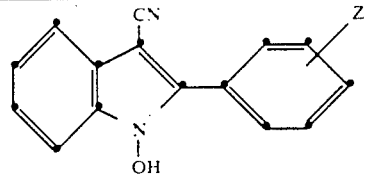

| Z | LB[a] | MD | AN | Ru | RH |
| --- | --- | --- | --- | --- | --- |
| H | 0 | 2 | 3(0) | 4(4) | 0 |
| 4-CH₃ | 1 | 0 | 1 | 2 | 0 |
| 4-Cl | 3 | 0 | 3 | 4 | 0 |
| 4-NO₂ | 2 | 0 | 1 | 4 | 0 |
| 4-CH=CHCN | 0 | 0 | 0 | 3(4) | 0 |
| 4-C(CH₃)₃ | 0 | 3(4)[b] | 1 | 1 | 0 |
| 4-COPh | 0 | 0 | 0 | 1 | 0 |
| 4-SO₂Ph | 0 | 0 | 0 | 0 | 0 |
| 4-OCH₃ | 1 | 0 | 1 | 1 | 0 |
| 4-CH=CHCO₂H | 0 | 0 | 0 | 0 | 4(4) |
| 4-CF₃ | 3(3) | 0 | 3 | 4(4) | 0 |
| 4-F | 0 | 0 | 0 | 3(4) | 0 |
| 4-OH | 1 | 0 | 0 | 3(2) | 0 |
| 4-CN | 0 | 0 | 0 | 1 | 0 |
| 4-CHO | 0 | 0 | 0 | 3(4) | 0 |
| 4-CH=NOH | 0 | 0 | 0 | 3(4) | 0 |
| 4-COCH₃ | 0 | 0 | 0 | 3(3) | 0 |
| 4-SO₂NH₂ | 0 | 0 | 0 | 0 | 0 |
| 4-CO₂H | 0 | 0 | 0 | 0 | 0 |
| 4-CH₂CO₂H | 0 | 0 | 0 | 0 | 0 |
| 3-NO₂ | 0 | 0 | 0 | 3(4) | 0 |
| 3-CF₃ | 2 | 2 | 1 | 4(4) | 0 |
| 2-NO₂ | 0 | 0 | 0 | 0 | 0 |
| 2-CF₃ | 0 | 0 | 0 | 0 | 2 |
| 3,4-diCl | 1 | 0 | 2 | 3 | 0 |

[a]LB = late blight on tomato
MD = powdery mildew on bean
AN = anthracnose on cucumber
Ru = leaf rust on wheat
RH = RH = Rhizoctonia on cotton
[b]Repeat test (value in parenthesis)

TABLE II

Wheat Leaf Rust
2-Aryl Series

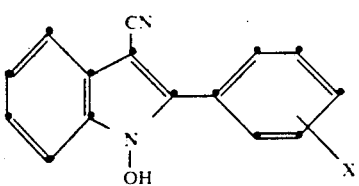

| Compound | X | EC$_{50}$[a] (ppm) |
|---|---|---|
| 1 | 4-NO$_2$ | 60 |
| 2 | H | 230 |
| 3 | 3-NO$_2$ | 50 |
| 4 | 2-NO$_2$ | 500 |
| 5 | 4-CF$_3$ | 280 |
| 6 | 3-CF$_3$ | 150 |
| 7 | 4-OCH$_3$ | 190 |
| 8 | 4-Cl | 350 |
| 9 | 4-CH=CHCN | 280 |
| 10 | 3,4-Cl$_2$ | 290 |
| 11 | 4-F | 150 |
| 12 | 4-CHO | 150 |
| 13 | 4-CH=NOH | 150 |
| 14 | 4-OH | 250 |
| 15 | 4-COCH$_3$ | 200 |
| 16 | 4-CN | 250 |

[a]Secondary test results - concentration at which 50% control of wheat leaf rust is observed.

TABLE III

Wheat Leaf Rust
Further Structural Exploration

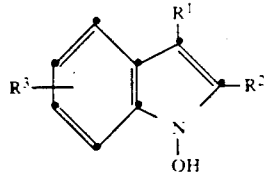

| Compound | R$^1$ | R$^2$ | R$^3$ | 1[a] | EC$_{50}$[b] (ppm) |
|---|---|---|---|---|---|
| 17 | CN | 4-NO$_2$Ph | 5,6-Cl$_2$ | 3(3) | 250 |
| 18 | CN | 4-NO$_2$Ph | 6-Cl | 3(4) | 125 |
| 19 | CN | Ph | 5,6-Cl$_2$ | 3(4) | 125 |
| 20 | CN | Ph | 6-Cl | 3(3) | 125 |
| 21 | CN | 2-Furanyl | H | 3(3) | 125 |
| 22 | CN | —CH=CH$_2$ | H | 3(4) | 125 |
| 23 | CN | 4-pyridyl | H | 3(3) | 125 |
| 24 | CN | 2-pyridyl | H | 4(3) | — |
| 25 | H | Ph | H | 3(4) | 100 |
| 26 | H | 4-ClPh | 6-Cl | 3(2) | 250 |

[a]Primary test results for wheat leaf rust at 500 ppm with repeat score in parenthesis.
[b]Secondary test results - Concentration at which 50% control of wheat leaf rust is observed.

TABLE IV

N-Hydroxy-3-cyano-2-ketoindoles

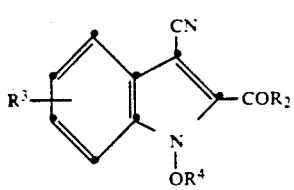

| Compound | R$^2$ | R$^3$ | R$^4$ | 1[a] |
|---|---|---|---|---|
| 28 | Ph | H | H | 3(4) |

TABLE IV-continued

N-Hydroxy-3-cyano-2-ketoindoles

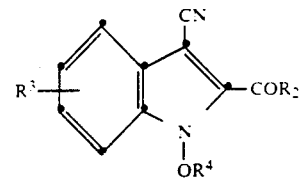

| Compound | R$^2$ | R$^3$ | R$^4$ | 1[a] |
|---|---|---|---|---|
| 28 | 3,4-Cl$_2$Ph | H | H | 4(3) |
| 29 | 4-MePh | H | H | 4(3) |
| 30 | 4-BrPh | H | H | 4(3) |
| 31 | 3-CF$_3$Ph | H | H | 4(0) |
| 32 | 4-ClPh | H | H | 4(3) |
| 33 | 3,4-(OMe)$_2$Ph | H | H | 4(0) |
| 34 | 4-OMePh | H | H | 4(0) |
| 35 | Ph | 5-Cl | H | 4(1) |
| 36 | t-Bu | H | H | 4(0) |

[a]Primary test results for wheat leaf rust at 500 ppm (repeat score in parenthesis).

TABLE V

Wheat Leaf Rust
Retesting

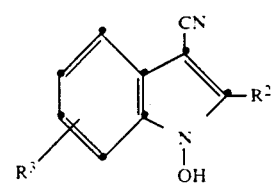

| Compound | R$^2$ | R$^3$ | EC$_{50}$[a] |
|---|---|---|---|
| 1 | 4-NO$_2$Ph | H | 100 |
| 2 | Ph | H | 450 |
| 3 | 3-NO$_2$Ph | H | 200 |
| 5 | 4-CF$_3$Ph | H | 250 |
| 6 | 3-CF$_3$Ph | H | 250 |
| 7 | 4-OMePh | H | 250 |
| 37 | 4-FPh | H | 250 |
| 38 | 4-CHOPh | H | 350 |
| 39 | 4-(CH=NOH)Ph | H | >>400 |
| 17 | 4-NO$_2$Ph | 5,6-Cl$_2$ | >400 |
| 18 | 4-NO$_2$Ph | 6-Cl | 250 |
| 19 | Ph | 5,6-Cl$_2$ | 300 |
| 20 | Ph | 6-Cl | 250 |
| 40 | 2-furanyl | H | 550 |
| 22 | CH=CH$_2$ | H | 400 |
| 23 | 4-pyridyl | H | >400 |
| 24 | 2-pyridyl | H | 200 |
| 31 | COPh | H | 400 |
| 32 | CO(3,4-Cl$_2$Ph) | H | >500 |
| 33 | CO(4-MePh) | H | >500 |
| 34 | CO(4-BrPh) | H | >500 |
| 35 | CO(3-CF$_3$Ph) | H | 300 |
| 36 | CO(4-ClPh) | H | >500 |
| 37 | CO(3,4-(OMe)$_2$Ph) | H | >500 |
| 38 | CO(4-OMePh) | H | 500 |
| 39 | COPh | 5-Cl | >500 |
| 40 | CO-t-Bu | H | 200 |
| 45 | CO-β-naphthyl | H | 0 |

[a]Secondary test results. Concentrations at which 50% control of wheat leaf rust is observed.
[b]Primary test results for wheat leaf rust at 500 ppm.

Three compounds of the invention having α-substituted-benzyl groups on the indole nucleus at the 2-position were tested for activity against *Botrytis cinerea* (BC) using peppers as the host (gray mold) and against *Puccinia recondita* (RU) using wheat as the host (wheat rust) by the following procedures:

Peppers and wheat are germinated and grown for one to three weeks (depending on species) in the greenhouse. Two pots representing two replicates of each plant species are placed in a flat such that each flat contains all the plants to be sprayed by one compound. The plants in each flat are sprayed to runoff at the rate of 135 ppm AI with either the test compound or a fungicide standard. As a control, check plants are sprayed with water. The plants are allowed to air dry two to three hours. After drying, the plants are sorted and grouped by plant species.

Plant pathogenic fungus *Botrytis cinerea*, is grown in the laboratory on appropriate media. Inoculum from the fungus is harvested and concentrations adjusted to predetermined levels. The obligate plant pathogenic fungus, *Puccinia recondita* f.sp. *tritici* is harvested from its host in the greenhouse and concentrations are adjusted to predetermined levels.

The plants previously treated with test compounds are sprayed with fungal inoculum and then placed in humidity chambers for a period of time previously determined to be optimum for development of each disease. After incubation, the plants are moved to the greenhouse, symptoms allowed to develop (one week), and the plants evaluated for disease intensity. The data reported in Table VI is the percent disease control at 135 ppm, and represents the average of the two replicates.

TABLE VI

| Compound | R2 | % Control at 135 ppm | |
|---|---|---|---|
| | | BC | RU |
| 46 | —C=N—Ph, Ph | 75 | 80 |
| 47 | —C=N—NH—Ph, Ph | 65 | 0 |
| 48 | —C=N—N(CH$_3$)$_2$, Ph | 50 | 0 |
| Standard (Botrytis = Benomyl)* | | 50 | — |
| Standard (Wheat rust = oxycarboxin)* | | — | 100 |
| Control (Water) | | 0 | 0 |

*Benomyl = Methyl 1-(butylcarbamoyl)-2-benzimidazolecarbamate
Oxycarboxin = 5,6-Dihydro-2-methyl-N-phenyl-1,4-oxathiin-3-carboxamide 4,4-dioxide The invention has been described in detail with particular reference to preferred embodiments thereof, but it will be understood that variations and modifications can be effected within the spirit and scope of the invention.

What is claimed is:

1. A process for controlling fungus which comprises contacting said fungus with a fungicidally effective amount of 1-hydroxyindole having the following formula

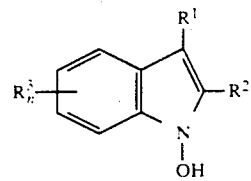

wherein,
R$^1$ is hydrogen, carbamoyl, t-butylcarbamoyl, dimethyl carbamoyl, carboxy, nitro, or cyano;
R$^2$ is selected from the group consisting of an alkenyl having 2-10 carbon atoms, an N-substituted-α-iminobenzyl, an unsubstituted or substituted aromatic group and an acyl having 2-16 carbon atoms;
R$_n^3$ is selected from the group consisting of halogen atoms; and
n is 0 to 4.

2. A process for controlling fungus which comprises contacting said fungus with a fungicidally effective amount of a 1-hydroxyindole having the formula of claim 1 wherein
R$^1$ is cyano or hydrogen,
R$^2$ is selected from the group consisting of alkenyl having 2-10 carbon atoms, N-substituted-α-iminobenzyl, an unsubstituted or substituted aromatic group, and acyl having 2-16 carbon atoms,
R$_n^3$ is selected from a group consisting of halogen atoms,
n is 0 to 4.

3. A process for controlling fungus which comprises contacting said fungus with a fungicidally effective amount of a 1-hydroxyindole having the formula of claim 1 wherein
R$^1$ is cyano,
R$^2$ is selected from the group consisting of 4-nitrophenyl, 3-nitrophenyl, 3-trifluoromethylphenyl, 4-methoxyphenyl, 4-fluorophenyl, 4-formylphenyl, 4-carbamoylphenyl, 2-furyl, vinyl, 4-pyridyl, 2-pyridyl, phenyl, 3,4-dichlorophenyl, 4-methylphenyl, 4-bromophenyl, 4-chlorophenyl, 3,4-dimethoxyphenyl, 4-methoxyphenyl, 3-trifluoromethylbenzoyl, 4-t-butylphenyl, hydroxyiminomethylphenyl, and α-(phenylimino)benzyl,
n is 0.

4. A process for controlling fungus which comprises contacting said fungus with a fungicidally effective amount of a 1-hydroxyindole having the formula of claim 1, wherein
R$^1$ is cyano,
R$^2$ is selected from the group consisting of phenyl and 4-nitrophenyl, and
n is 0.

5. A process for controlling fungus which comprises contacting said fungus with a fungicidally effective amount of a 1-hydroxyindole having the formula of claim 1 wherein
R$^1$ is hydrogen,
R$^2$ is selected from the group consisting of phenyl, 4-nitrophenyl and 4-chlorophenyl, and
R$_n^3$ where n=0-2 and R is selected from chloro, so that R$_n^3$ represents chloro, dichloro or no substituents replacing hydrogen for R$^3$, and n is 0, 1 or 2.

6. A process according to claim 1 wherein R$^2$ is a meta-substituted phenyl group.

7. A process according to claim 1, wherein R$^2$ is a para-substituted phenyl group.

8. A process according to claim 1 wherein R$^2$ is selected from the group consisting of 3-nitrophenyl and 4-nitrophenyl.

9. The process according to claim 1 wherein said fungus is wheat leaf rust.

* * * * *